United States Patent
Qi

(10) Patent No.: US 6,308,342 B1
(45) Date of Patent: Oct. 30, 2001

(54) KIND OF MAN'S BRIEFS AND LINING OF THE BRIEFS

(76) Inventor: Xiaoming Qi, No. 1118, Building #19, Region #12, Heping Jie, Chaoyang Dist., Beijing (CN), 100013

( * ) Notice: Subject to any disclaimer, the term of this patent is extended or adjusted under 35 U.S.C. 154(b) by 0 days.

(21) Appl. No.: 09/647,000
(22) PCT Filed: Jun. 3, 1999
(86) PCT No.: PCT/CN99/00075
  § 371 Date: Sep. 22, 2000
  § 102(e) Date: Sep. 22, 2000
(87) PCT Pub. No.: WO99/63845
  PCT Pub. Date: Dec. 16, 1999

(30) Foreign Application Priority Data

Jun. 11, 1998 (CN) .................................................. 98205905

(51) Int. Cl.$^7$ ...................................................... A41D 1/00
(52) U.S. Cl. ................................................... 2/403; 2/400
(58) Field of Search ............................... 2/400, 403, 405; 602/67, 68, 69, 70, 71, 73

(56) References Cited

U.S. PATENT DOCUMENTS

| | | | |
|---|---|---|---|
| 2,027,622 | * 1/1936 | Stam | 602/69 |
| 2,050,410 | * 8/1936 | Baer | 602/69 |
| 2,138,481 | * 11/1938 | Chatfield | 2/403 |
| 2,624,336 | * 1/1953 | Hansley | 2/403 |
| 3,080,869 | * 3/1963 | Alberts | 2/155 |
| 3,207,155 | * 9/1965 | Casey | 2/403 |
| 3,499,442 | * 3/1970 | Steinmetz | 2/403 |
| 5,524,298 | * 6/1996 | Plunkett | 2/403 |
| 5,870,779 | * 2/1999 | Heron | 2/403 |
| 5,974,592 | * 11/1999 | Tabrizi | 2/400 |

* cited by examiner

Primary Examiner—Gloria M. Hale
(74) Attorney, Agent, or Firm—Intellectual Property Law Group LLP; Otto O. Lee; Takashi Hashimoto

(57) ABSTRACT

Men's briefs and lining of the briefs comprising a waistband section, a front section, and a back section, wherein a support belt is connected to the front section. The bottom of the support belt has an arc shape and forms a bag section between the bottom of the tightening position of the scrotum and the upper ends of the wearer's legs. The bag section formed at the bottom of the front section facilitates the supporting and holding of the scrotum. The two ends of the support belt flare up and are connected with the front section and the waistband section to facilitate the stability of the support belt and the supporting force. The support belt itself can be adjusted easily by adjusting the width of the flared mouth of the support belt, the length of the support belt, or the tension of the elastic ribbon. Thus, with adjustment by the wearer, the proper support position and a comfortable supporting force can be attained.

9 Claims, 5 Drawing Sheets

KIND OF MAN'S BRIEFS AND LINING OF THE BRIEFS

BACKGROUND

This invention is related to a special kind of protective underwear, and specifically, it is a type of men's briefs and lining of the briefs.

Medical science and practical experience have proven that a man's testes will hang down as the scrotum loosens at maturity. While it is natural that the testes hang down to a certain extent, they tend to be pressed and pushed together by the upper ends of a man's legs. This happens most often when a man is in a sitting position. This problem will not only make a man uncomfortable but will also affect his health adversely.

Until now, the comfort of men's briefs were mainly dependent upon the comfort, while being worn, of the material used to make them; such as the softness, lightness, and sweat absorption performance of cotton, etc. Therefore, most of the currently available brief designs are based on a selection of materials that are comfortable to wear. However, even briefs made with soft and comfortable materials, whether cut in a triangular shape or in a rectangular shape, do not act to functionally support and hold the scrotum above the upper ends of a man's legs. Therefore, they do not solve the above-mentioned problem of the discomfort caused to a man when his scrotum is pressed between his legs.

The purpose of this invention is to provide a new kind of men's briefs and lining of the briefs, which can control the position of the scrotum by supporting and holding the scrotum above the upper ends of a man's legs. Thus, this invention prevents the discomfort caused to a man by his testes being pressed and pushed together.

SUMMARY

The technical part of this invention relies on a support belt. This support belt is added to the front section of a pair of men's briefs. The bottom of the support belt is in the shape of an arc and forms a bag of material for holding the scrotum in the front section of the brief, formed from the bottom portion of the front section of the material of the brief. Both ends of the support belt have a flared shape and arc upwards. The support belt is connected to the front section of the briefs and the waistband for the stability of the support belt and to provide the support force. The support belt can be adjusted easily by changing the width of the flared mouth of the support belt, the length of the support belt, or the tension of the support belt. Thus, the proper support position and a comfortable support force can be achieved by adjustment of the support belt.

When the men's briefs and briefs lining are worn, the bottom tightening section of the support belt is positioned between the bottom of the scrotum and the groins, above the upper ends of the legs, by adjusting the support belt. Thus, the support belt resists the hanging down of the scrotum. While the support belt resists the hanging of the scrotum, it also offers a support function together with a bag of material to hold the scrotum, which is formed by the support belt and the front section. The structural combination of the support belt, the front section of the briefs, and the waistband section can effectively control the extent of the hanging down of the scrotum and prevent the testes from being pressed together by the upper ends of the legs.

This invention has many advantages. Because, in one of the embodiments, only a support belt is added to the front section of a pair of men's briefs, its structure is very simple. Thus, the hanging down of the scrotum is restrained by the support belt. The performance of the briefs lining's breatheability, ventilation, and temperature reducing characteristics in the area of the upper ends of a man's legs are improved significantly by this invention. The process of attaching the support belt to the briefs is very easy since the support belt and the front section of the briefs are connected together. Additionally, the support belt does not require that special materials be used for the briefs since this invention is intended to provide the support function.

DRAWINGS

DETAILED DESCRIPTION OF THE INVENTION

Embodiment 1

Figure 1:
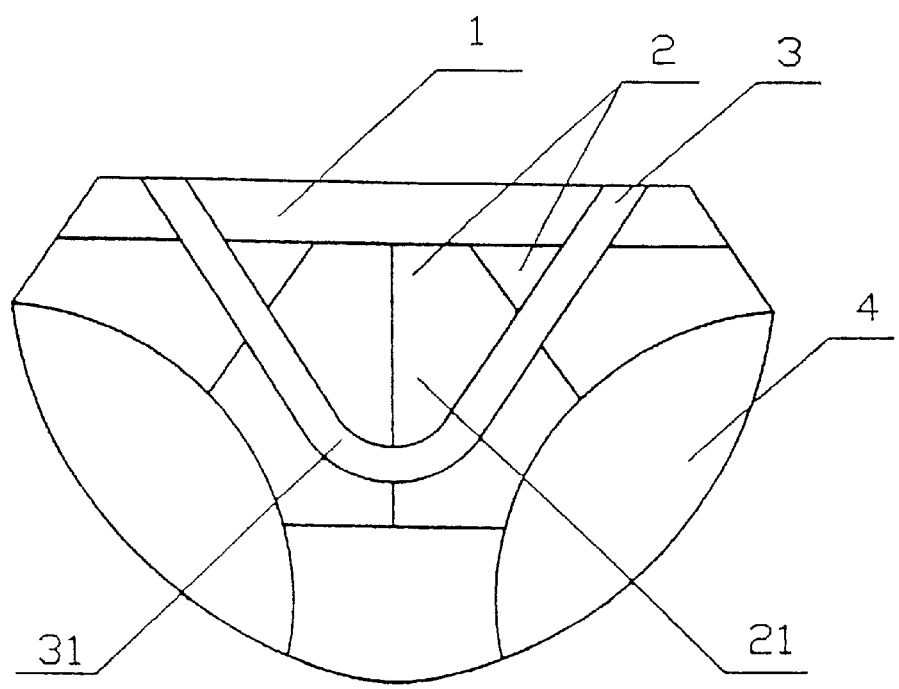
FIG. 1 shows the structural illustration of the invention as used with triangular briefs and lining.
Figure 2:
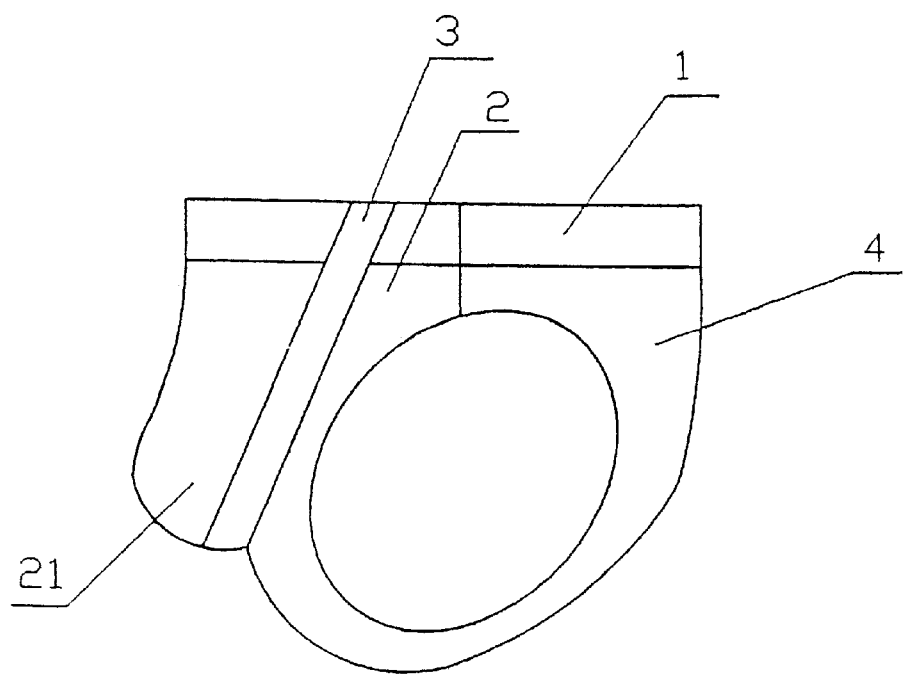
FIG. 2 shows the side view of the triangular briefs and lining with this invention while being worn.

As shown in FIGS. 1 and 2, this invention comprises a waistband section (1), a front section (2), a support belt (3), and a back section (4). The support belt (3) is connected to the front section (2). Both ends of the support belt (3) have an upwards flared shape, connected with the front section (2) and the waistband section (1) of the front section so as to provide stability for the support belt (3). The bottom of the support belt has an arc shape, and it forms a bag together with the bottom portion of the front section (2) to support and hold the scrotum.

Because the support belt (3) part of this invention needs a stable means of connection to the briefs, different means of connection can be used according to the different brief materials used. In addition, the support belt itself should be adjusted according to the wearer's individual requirements for support and position.

For example, as seen in the structure shown in embodiment 1 (FIGS. 1–4), the front section (2) of the briefs is made of a popular kind of soft knitted cloth. The support belt (3) is made of a low elasticity material. The entire support belt (3) is attached to the front section (2) and the waistband section (1), and a bag section (21) is formed by the material of the front section (2) surrounded by the arc section (31) of the bottom of the support belt (3). The bottom of the bag section (21), which is surrounded by the support belt (3), should be located between the bottom of the scrotum and the upper ends of the legs. With the above-mentioned structure, when the briefs are worn, the bottom of the support belt is between the bottom of the scrotum and the groins, above the upper ends of the legs, thus forming an obstacle to the hanging down of the scrotum. While resisting the hanging down of the scrotum, the support belt (3), the bag formed by the support belt (21), and the front section (2) offer support and hold the scrotum, above the upper ends of the legs of the wearer.

In one variation of embodiment 1, the support belt (3) can also be made of an elastic material. The bag section (21) is formed by the bottom of the front section (2) and the elasticity of the support belt (3), where the support belt (3) connects to the front section (2) and the waistband section (1), along the entire length of the support belt (3). In another variation of embodiment 1, when the support belt (3) is connected with the front section (2) and the waistband section (1), an elastic belt (31) can be added onto the support belt (3) along the entire length of the support belt (3), between the front section (2) and the waistband section (1).

In the above mentioned embodiment 1, the means of connection for the entire length of the support belt (3) can be designed to different specifications according to different body types so as to meet individual requirements.

FIG. 2 is a second illustration of embodiment 1 of this invention, shown while being worn. When it is worn, the tightening portion of the bottom of the support belt (3) is between the bottom of the scrotum and the groins, above the upper ends of the wearer's legs. Thus, it resists the hanging down of the scrotum. While resisting the hanging down of the scrotum, the support belt (3), with the bag (21) formed by the support belt (3) and the front section (2), holds the scrotum. Since the support belt (3) is adjustable, the adjustment of the support belt (3) can control the extent of the hanging down of the scrotum, and thus protects the testes against being pressed together by the upper ends of the wearer's legs.

In summary of the above-mentioned description of embodiment 1, since only a support belt (3) is added to the front section (2) of a man's briefs, the structure of this invention is very simple and will not make wearing of the briefs being less comfortable. Additionally, since the structure of the support belt (3) can effectively restrain the hanging down of the scrotum, the breatheability, ventilation, and temperature reduction in the area of the upper ends of the wearer's legs are significantly improved. Since the support belt (3) and the front section (2) are attached together, the process of putting on the invention is very easy. Moreover, because this invention is intended to provide a supportive function, the support belt (3) does not need to be made of any special material.

Embodiment 2

Figure 5:
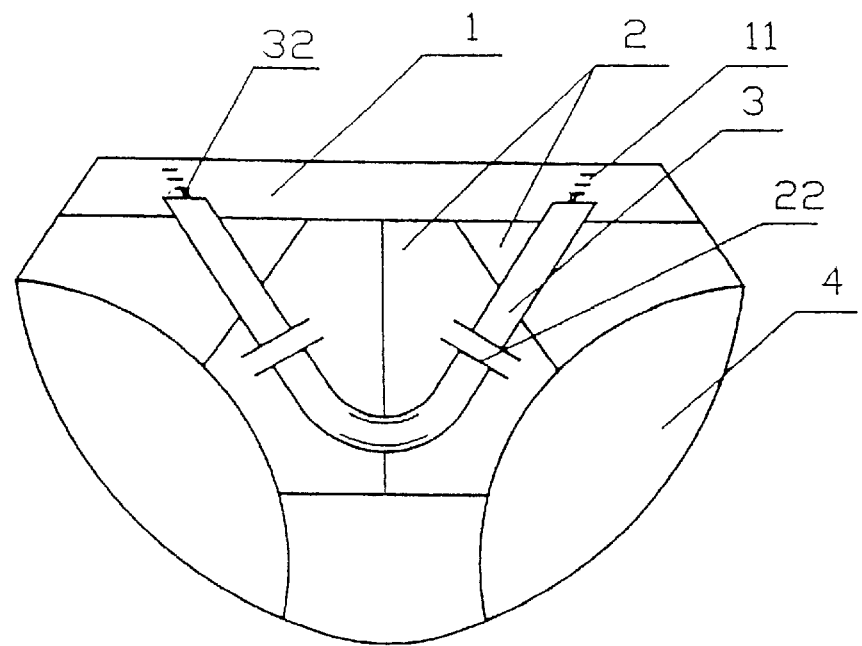
FIG. 5 shows the structural illustration of the second embodiment of this invention.

The second embodiment of this invention is shown in FIG. 5. In this embodiment, the support belt (3) is connected to the front section (2) and the waistband section (1) only at three points. The first point of connection is at arc section (31), the bottom of the support belt is attached to the extreme bottom of the bag section of the front section (2). This ensures stability to the bottom section (33) of the support belt (3). The second and third points of connection are at the top of the flared mouth of the support belt (3), at these points the support belt is connected to the waistband section (1). In order to make the support and position of the support belt (3) comfortable, the wearer should adjust the support belt (3) when the briefs are put on. Additionally, a length adjustment device can be installed on the support belt (3), the support and position of the support belt (3) can be controlled by adjusting the length of the support belt. Various existing length adjustment methods can be utilized in the length adjustment device. For example, several hooks (32) are installed at either end of the support belt (3), and several holes (11) are made in a longitudinal direction on the waistband section (1) as shown in FIG. 5. The length of the support belt can be adjusted by hooking the hooks (32) into the different holes, up and down the waistband section (1), so as to adjust the supporting force. In addition, other popular length adjustment devices such as tabs, nylon hook and loop fasteners, and buttons etc. can also be used for the length adjustment device of this invention. The support belt (3) can also be made of two segments, with several holes being made on one segment, while several hooks being installed on the corresponding segment. This method of length adjustment allows for the length of the support belt (3) itself to shortened or lengthened.

In this embodiment, since the support belt (3) is connected to the front section (2) and the waistband section (1) at three points, a positioning device is installed between the top and bottom connection is points of the support belt (3) so as to stabilize the portion of the support belt (3) between the top and bottom connection points on the front section (2). The positioning device can be a set of holes (22) on the front section (2), allowing the support belt (3) to penetrate through the set of holes (22) and form a stable integration with the front section (2). The positioning device can also be a tab installed on the front section (2), the width of the mouth of the tab would be slightly greater than the width of the support belt (3) so as to not allow the support belt (3) to move in a transverse direction.

With the above-mentioned structure, this embodiment can be easily and well adjusted for the wearer. At the time of the first use, the wearer can make the adjustments according to his individual requirements for comfort, and thereafter no further adjustments will be needed. Thus, the structure of this embodiment is highly adaptable and can well suit the needs of various wearers.

Embodiment 3

Figure 6:
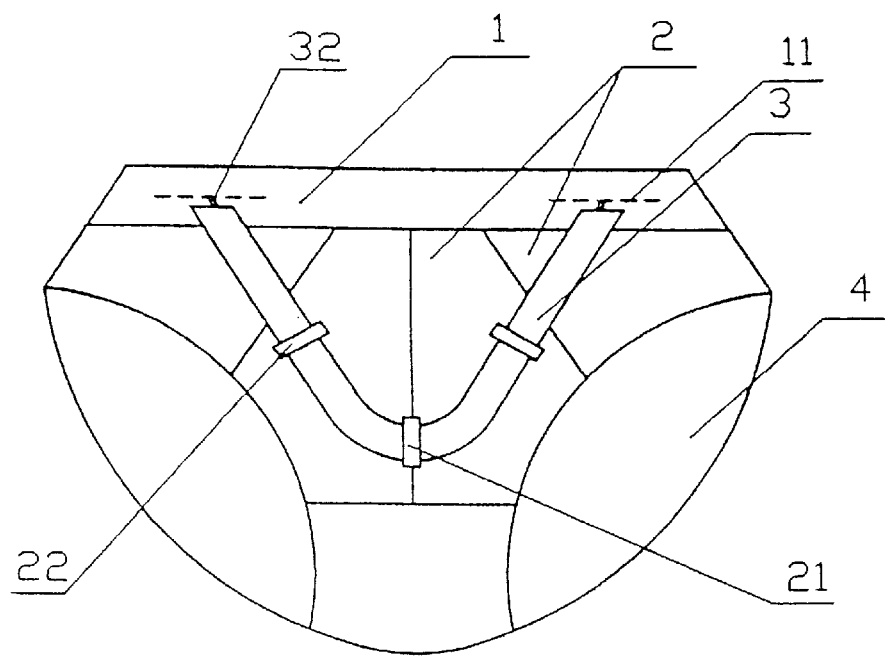
FIG. 6 shows the structural illustration of the third embodiment of this invention.

Embodiment 3 is shown in FIG. 6, which is similar to FIG. 5 for embodiment 2. As in embodiment 2, the support belt (3) is connected to the front section (2) and the waistband section (1) of the briefs at three points. However, the difference between embodiment 2 and embodiment 3 is that section (31) of the bottom of the support belt (3) is connected to the bottom of the bag section of the front section (2) with a tab device (21) to ensure stability of the bottom of the support belt (3). Additionally, the top flared mouth of the support belt (3) is connected to the waistband section (1), and the support belt (3) can be adjusted by the wearer while putting on the briefs so as to make the supporting position of the support belt (3) comfortable. To adjust the width of the flared mouth at the top of the support belt (3) in this embodiment, several holes (11) can be made horizontally along the waistband section (1), and several hooks (32) can be installed at the flared mouth end of the support belt (3). Thus, the width of the flared mouth end of the support belt can be adjusted by changing the hooking position of the hook (32). When the width of the flared mouth of the support belt (3) is great, the arc section at the bottom of the support belt (3) will be lifted up; however, when the width of the flared mouth end of the support belt is small, the section at the bottom of the support belt (3) will be lowered. Thereby, adjustments of the support belt (3) to high or low positions can be made by the wearer. Another option is to have buttons at different positions on the waistband section or other connection points that can also be used to adjust the width of the flared mouth end of the support belt (3).

Embodiment 4

Figure 7:
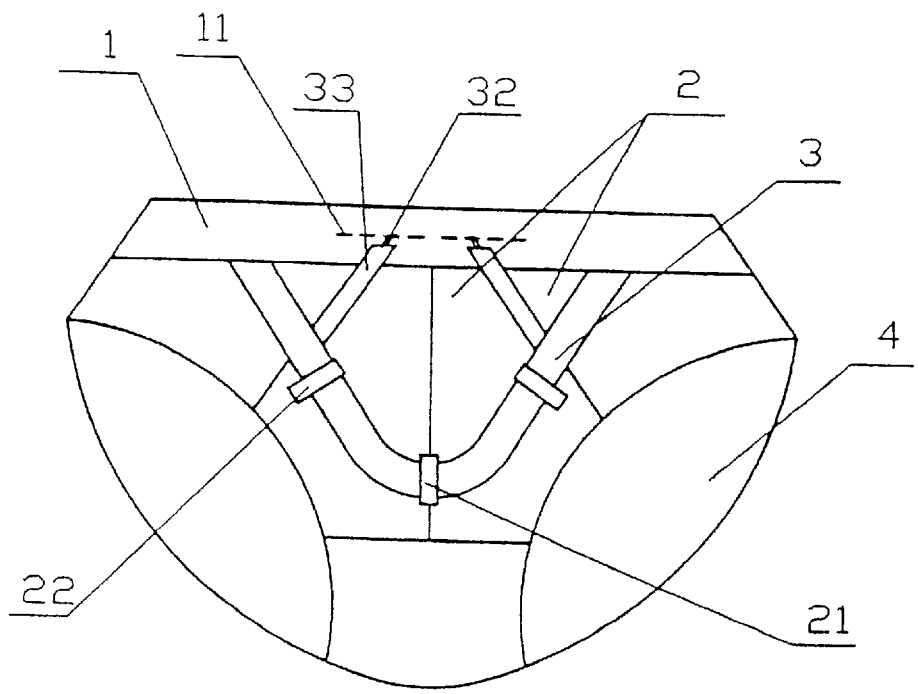
FIG. 7 shows the structural illustration of the fourth embodiment of this invention.

In the fourth embodiment of this invention, shown in FIG. 7, the structure of this embodiment is nearly identical to that of the embodiment 3. The difference between embodiment 3 and embodiment 4 is that the flared mouth end of the support belt (3) in embodiment 4 (FIG. 7) is adjusted by two auxiliary belts (33) attached to the support belt (3). The auxiliary belt can change the width of the flared mouth of the support belt (3) by pulling the support belt inward or not.

Embodiment 5

Figure 8:
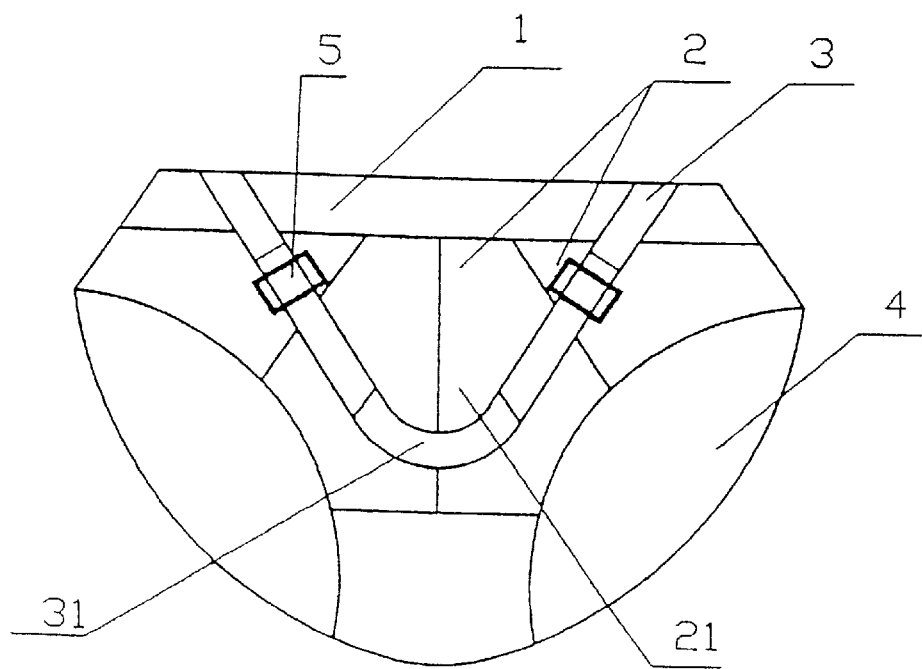
FIG. 8 shows the structural illustration of the fifth embodiment of this invention.

In embodiment 5, as shown in FIG. 8, only the arc section (31) at the bottom of the support belt (3) is made of an elastic material (such as elastic ribbons, etc.). The arc section (31) can be connected to the bottom of the front section (2). With the elasticity of the arc section (31), a bag section (21) can be formed by tightening the arc section (31) at the bottom of the front section (2). Various adjustment structures for the support belt (3), described previously, offer the wearer the ability to adjust the supporting force of the support belt (3), and thus control the extent of the hanging down of the scrotum.

The support belt (3) is attached to the front section (2) and the waistband section (1) with the mouth ends flared. The bottom section can be loosened, and a length adjustment device (5) installed at a proper position on the loosened section of the support belt (3). The previously described various length adjustment devices are all suitable for this embodiment. The function of the length adjustment device (5) is to adjust the supporting force according to the wearer's individual comfort, by controlling the extent of the hanging down of the scrotum.

With the above description, this invention can fulfill various means of connections and adjustments, and its aim is to make users with different demands feel more comfortable while wearing this kind of man's briefs. The various above-mentioned connection methods and adjustment methods for the supporting force in this embodiment are used to describe the invention in embodiment 5 only, but are not limited only to this embodiment of this invention.

Embodiment 6

Figure 9:
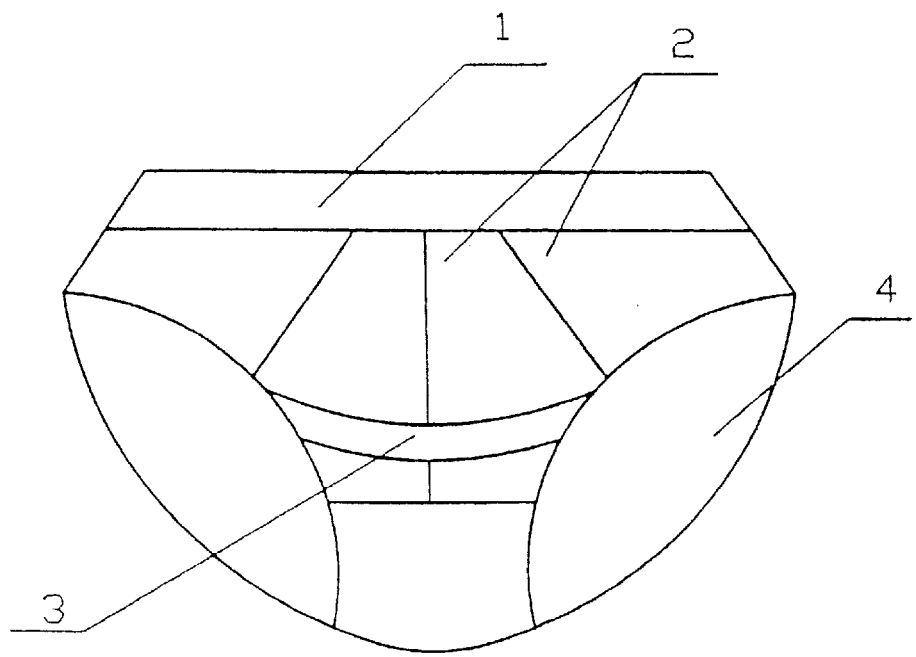
FIG. 9 shows the structural illustration of the sixth embodiment of this invention.
Figure 10:
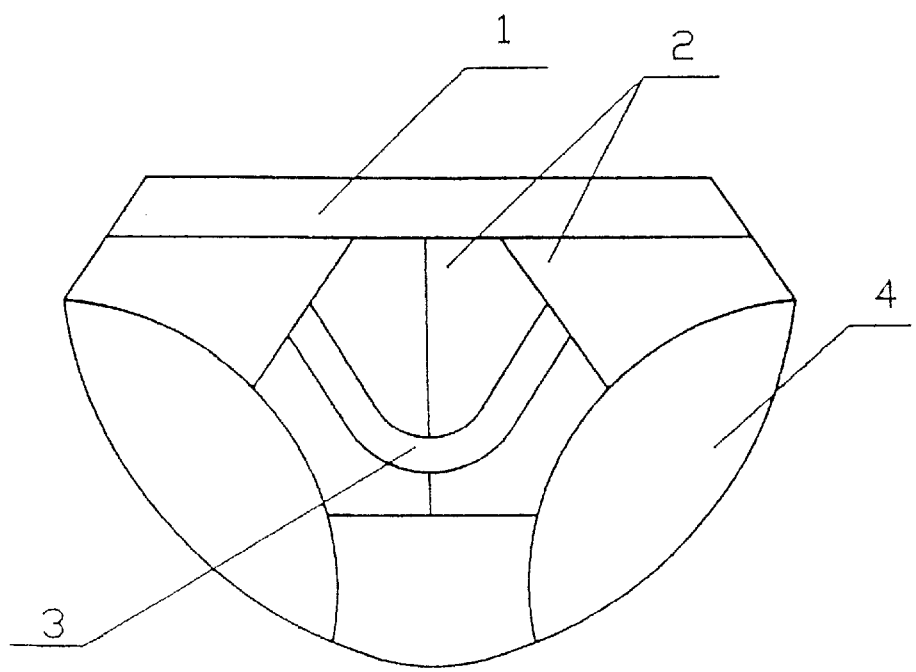
FIG. 10 shows the structural illustration of a variation of the sixth embodiment of this invention.

Embodiment 6 is shown in FIG. 9. The support belt (3) has an arc shape and is located between the two leg openings in the briefs, at the bottom of the front section (2), and is affixed to the front section (2). The support belt can be designed to different specifications. The support belt (3) can also be affixed to the seam of the front section (2) where the seam runs between the waistband (1) and the leg opening (4), as shown in FIG. 10. This embodiment is designed based on the popular triangular briefs style.

In the above-mentioned embodiment, if the front section (2) of the triangular briefs has a double-layer of fabric structure (such a double-layer structure is popular, but it is not shown in the figure), the support belt (3) can penetrate through the double-layer of fabric in the front section (2) into the double-layer structure after the support belt's bottom is affixed to the front section (2). Thus, the above-mentioned various connections, positioning, and adjustment devices can be connected into the interlayer of the double-layer fabric structure of the front section (2). This variation of embodiment 6 can eliminate discomfort for the wearer due to the thick front section of the briefs while the support belt (3) functions to support the wearer's scrotum.

Embodiment 7

Figure 3:
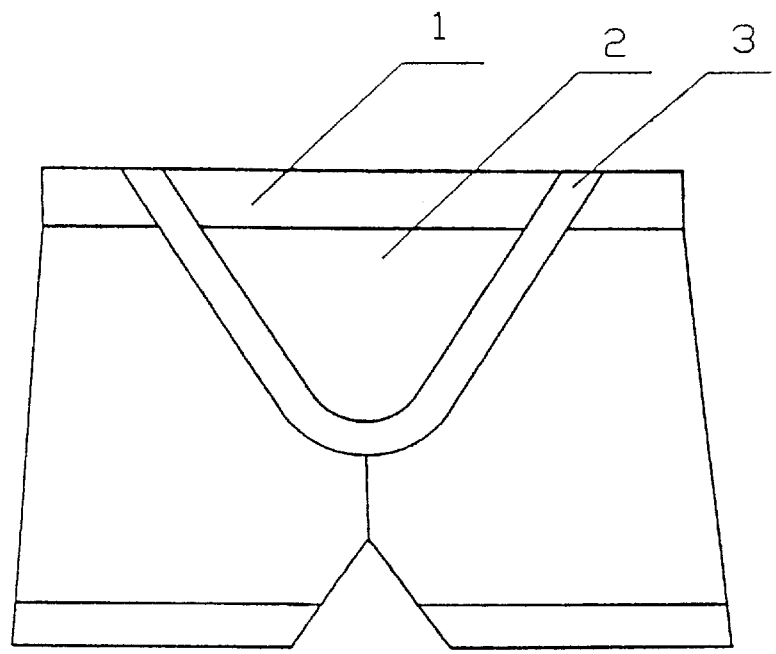
FIG. 3 shows the structural illustration of the invention as used with rectangular briefs and lining.
Figure 4:
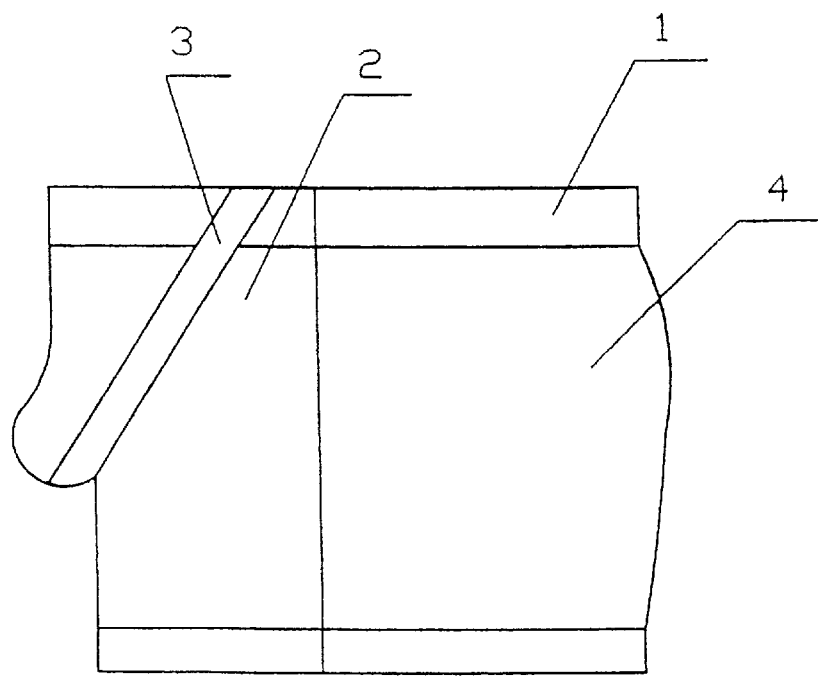
FIG. 4 shows the side view of the rectangular briefs and lining with this invention while being worn.

In embodiment 7, as shown in FIGS. 3 and 4, the support belt (3) is connected to the front section (2) and the waistband section (1) of a type of rectangular man's briefs and lining. A bag section (21) is formed by the support belt (3) and the portion of the front section (2) which is surrounded by it. The attachment method is the same as that in the embodiment 1 and thus is not stated again. The support function of this embodiment is identical to that of embodiment 1.

What is claimed is:

1. A men's briefs and lining of the briefs, comprising:
   a. a waistband section,
   b. a front section,
   c. a back section,
   d. a support belt having:
      i. a bottom,
      ii. a first end,
      iii. a second end, and
   e. a bag section formed by the support belt and the front section,
   wherein the first end and the second end of the support belt are flared in an upward direction,
   wherein the bottom of the support belt has an arc shape, and
   wherein the support belt is attached to the front section.

2. A men's briefs and lining of the briefs, comprising:
   a. a waistband section;
   b. a front section;
   c. a back section;
   d. a support belt having:
      i. a bottom,
      ii. a first end,
      iii. a second end, and
   e. a bag section formed by the support belt and the front section,
   wherein the first end and the second end of the support belt are flared in an upward direction,
   wherein the bottom of the support belt has an arc shape,
   wherein the support belt is attached to the front section,
   wherein said support belt has a length between a first end and a second end, and
   wherein the length of the support belt is adjustable.

3. A men's briefs and lining of the briefs, comprising:
   a. a waistband section;
   b. a front section;
   c. a back section;
   d. a support belt having:
      i. a bottom,
      ii. a first end,
      iii. a second end, and
   e. a bag section formed by the support belt and the front section,
   wherein the first end and the second end of the support belt are flared in an upward direction,
   wherein the bottom of the support belt has an arc shape,
   wherein the support belt is attached to the front section, and wherein a width of a flared mouth of the support belt is adjustable.

4. The men's briefs and lining of the briefs as described in claim 1 or claim 2, wherein the support belt has an elastic structure so as to adjust a supporting force from the support belt.

5. The men's briefs and lining of the briefs, as described in claim 1 or claim 2, wherein a length adjustment device is installed on the support belt so as to adjust a supporting force from the support belt.

6. The men's briefs and lining of the briefs as described in claim 2, wherein the support belt has an elastic structure so as to adjust a supporting force from the support belt.

7. The men's briefs and lining of the briefs, as described in claim 2, wherein a length adjustment device is installed on the support belt so as to adjust a supporting force from the support belt.

8. The men's briefs and lining of the briefs as described in claim 3, wherein the support belt has an elastic structure so as to adjust a supporting force from the support belt.

9. The men's briefs and lining of the briefs, as described in claim 3, wherein a length adjustment device is installed on the support belt so as to adjust a supporting force from the support belt.

* * * * *